United States Patent [19]
Holmberg

[11] Patent Number: 5,589,586
[45] Date of Patent: Dec. 31, 1996

[54] NUCLEOSIDES ATTACHED TO A SOLID SUPPORT THROUGH A 3'-SILYL LINKAGE AND THEIR USE IN OLIGONUCLEOTIDE SYNTHESIS

[75] Inventor: Lars Holmberg, Uppsala, Sweden

[73] Assignee: Pharmacia LKB Biotechnology AB, Uppsala, Sweden

[21] Appl. No.: 915,820

[22] PCT Filed: Nov. 25, 1991

[86] PCT No.: PCT/SE91/00797

§ 371 Date: Jul. 24, 1992

§ 102(e) Date: Jul. 24, 1992

[87] PCT Pub. No.: WO92/09615

PCT Pub. Date: Jun. 11, 1992

[30] Foreign Application Priority Data

Nov. 26, 1990 [SE] Sweden ................................. 9003743

[51] Int. Cl.$^6$ ................................................. C07H 21/00
[52] U.S. Cl. ................... 536/25.3; 536/25.33; 536/25.34
[58] Field of Search ............................................ 536/25.3

[56] References Cited

FOREIGN PATENT DOCUMENTS

| | | | |
|---|---|---|---|
| 0035719 | 9/1981 | European Pat. Off. ............ | 536/25.30 |
| 0208599 | 1/1987 | European Pat. Off. ............ | 536/25.30 |
| 2529892 | 1/1984 | France ................................. | 556/407 |

OTHER PUBLICATIONS

Angew, Chem. Int. Ed. Engl., vol. 28, 1989 Joachim W. Engels et al.: "Gene Synthesis", see p. 716–p. 734.

Gait, *Oligonucleotide Synthesis. A Practical Approach*, IRL Press, Washington, DC, 1984, see p. 46–47, 85–86 and 114–115.

Kumar et al., "Improvements in Oligodeoxyribonucleotide Synthesis: Methyl N,N–Dialkylphosphoramidite Dimer Units of Solid Support Phosphite Methodology,"*J. Org. Chem.*, 49, 4905–4912 (1984).

DeBart et al., "Sugar Modified Olginucleotides: II. Solid Phase Synthesis of Nuclease Resistant α–Anomeric Uridylates as Potential Antisense Agents," *Tett. Lett.*, 31(25), 3537–3540 (1990).

Hayakawa et al., "The Allylic Protection Method in Solid–Phase Oligonucleotide Synthesis. An Efficient Preparation of Solid–Anchored DNA Oligomers,"*J. Am. CHem. Soc.*, 112, 1691–1696 (1990).

*Primary Examiner*—Douglas W. Robinson
*Assistant Examiner*—L. Eric Crane
*Attorney, Agent, or Firm*—Birch, Stewart, Kolasch & Birch

[57] ABSTRACT

Support system for the synthesis of oligonucleotides wherein the first nucleoside is bound to the support via a silylether linkage, especially of the formula

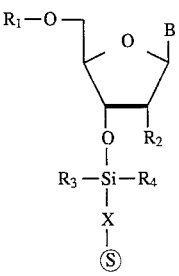

wherein
B is a nucleoside or deoxynucleoside base.
$R_1$ is a protecting group.
$R_2$ is —H, —OH, or —$OR_5$, in which $R_5$ is a protecting group.
$R_3$, $R_4$ and X each represent alkyl, aryl, cycloalkyl, alkenyl, aralkyl, cycloalkylalkyl, alkyloxy, aryloxy, cycloalkyloxy, alkenyloxy, aralkyloxy.
S is a solid support, whereby not more than one of $R_3$, $R_4$ and X represent alkyloxy, aryloxy, cycloalkyloxy, alkenyloxy, aralkyloxy or cycloalkylalkyloxy.

9 Claims, 2 Drawing Sheets

NUCLEOSIDES ATTACHED TO A SOLID SUPPORT THROUGH A 3'-SILYL LINKAGE AND THEIR USE IN OLIGONUCLEOTIDE SYNTHESIS

The present invention relates generally to oligonucleotide synthesis and, particularly, to a new and improved way of attaching the first nucleoside to the solid support that enables oligonucleotides to be more easily and effectively synthesized, deprotected and purified.

Oligonucleotides are polymers built up by polycondensation of ribonucleoside (RNA) or deoxyribonucleoside (DNA) phosphates. The availability of synthetic oligonucleotides has revolutionized molecular biology research. Some of the most important applications of synthetic oligonucleotides are as primers for DNA-sequencing, as primers in the polymerase chain reaction (PCR), as probes for the identification and/or isolation of genes, as building blocks for gene synthesis, and as potential anti-viral compounds in the form of anti-sense oligonucleotides (Ref. 1–3).

Oligonucleotides can be assembled by repetitive addition of nucleotide monomers using solid-phase methods (Ref. 4). Since the introduction of solid-phase synthesis by *Merrifield* (Ref. 5), the following requirements have been worked out: (1) The solid support must be insoluble and preferably unswellable in the solvent used. (2) Functional groups on the solid support must allow covalent binding of the first nucleoside in a reproducible manner. (3) The solid support must be chemically inert to all reagents used during synthesis and deprotection.

A number of materials have been tested but the most commonly used today are controlled pore glass beads (CPG), silica, or polystyrene beads (Ref. 4).

BRIEF DESCRIPTION OF THE DRAWINGS

The first 5'-protected nucleoside is attached to the support via an alkylamine spacer through the 3'-hydroxyl function. This is normally done by condensation of protected nucleoside 3'-succinate esters with the support-bound alkylamine (see FIG. 1).

This means that four different supports are used, one for each nucleoside (A,C,G,T). Synthesis of oligonucleotides is today almost exclusively carried out by fully automated instruments, by the so called "Gene Machines".

Figure 1:
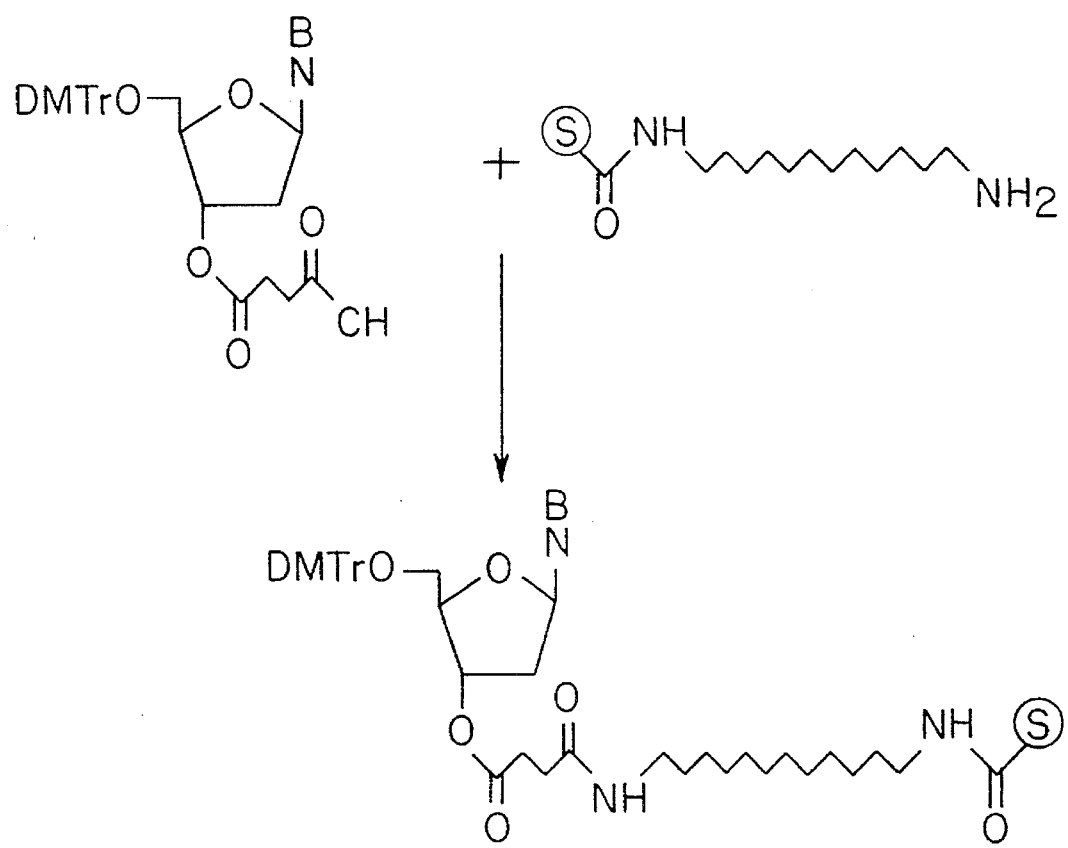
Figure 2:
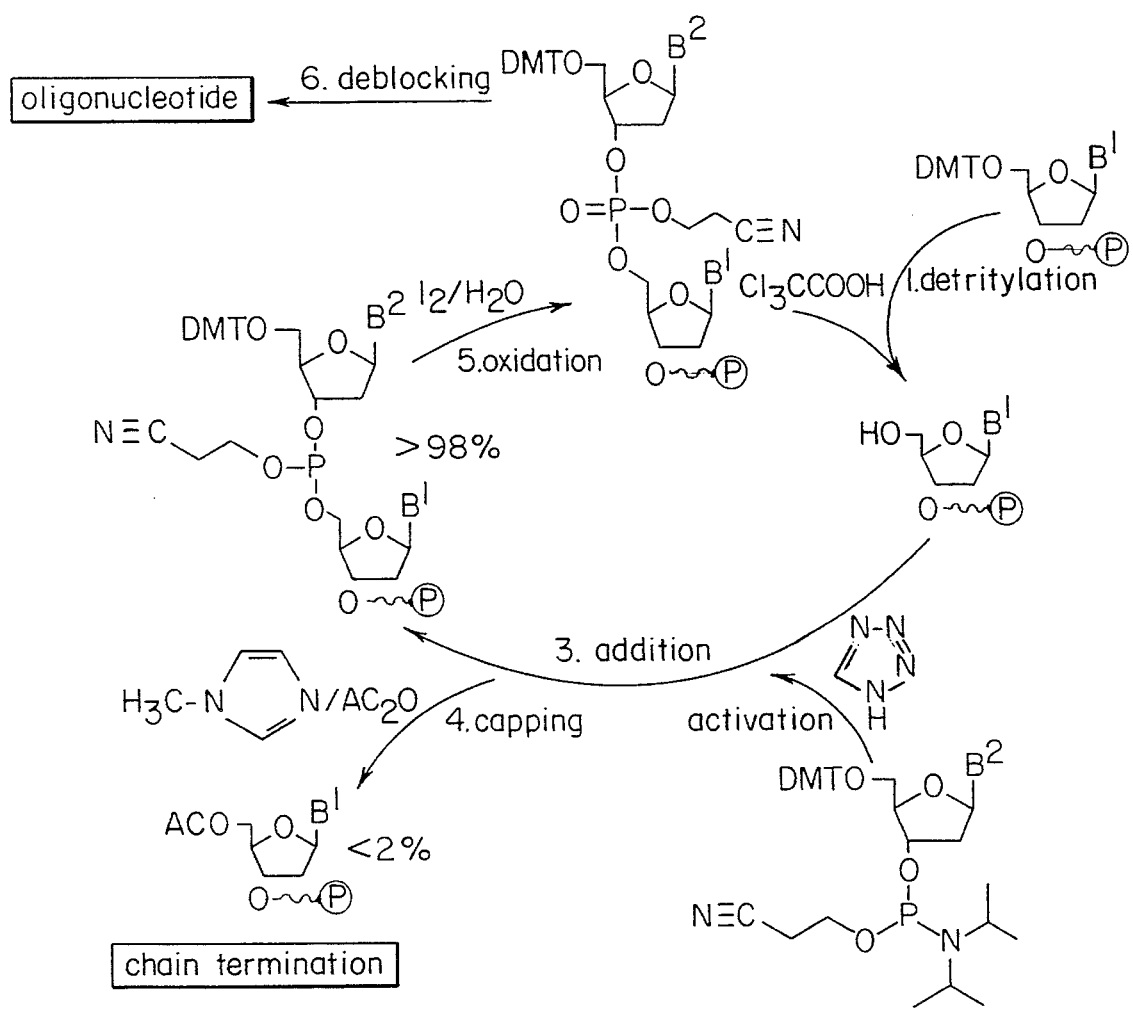

The steps needed to carry out the addition of one nucleotide monomer to the growing chain on the so-lid support using the phosphoramidite method (Ref. 6–8) can be summarized as described below in what is normally referred to as the synthesis cycle, (see FIG. 2). Other methods differ mainly in the nature of the phosphorous moiety (e.g. Phosphotriester (Ref. 11), H-phosphonate (Ref. 9–10) method).

1. Deprotection of the 5'-hydroxyl group in order to generate the parent hydroxyl compounds. This is normally done by treatment of the support with di- or trichloroacetic acid in an organic solvent (for removal of DMTr).

2. The support is washed in order to remove traces of acid.

3. The 5'-hydroxyl group is reacted with the 3'-phosphoramidite moiety of a properly protected incoming nucleotide (A,C,G or T) in the presence of an activator (e.g. tetrazole) to form a 3'-5'-phosphite triester.

4. Excess reagents are removed by washing with an appropriate solvent.

5. Unreacted 5'-hydroxyl groups are blocked as acetates (capping).

6. The capping reagents are removed by washing.

7. The phosphite triester is then oxidized to the corresponding phosphate triester. This is normally done by the action of aqueous iodine.

8. The oxidation reagents are removed by washing.

This process is repeated until the desired oligonucleotide sequence has been synthesized. The difference between the cycles is the nucleotide monomer used for coupling in step 3.

The efficiency of this process is very high. Often, coupling efficiencies above 99% can be obtained. An inherent problem though associated with any polymer supported, repetitive synthesis is the stability of the growing oligonucleotide chain to the various reagents that are used during synthesis. One particularly troublesome problem is that of acid-catalysed depurination of deoxyadenosine (Ref. 12), and to a lesser extent deoxyguanosine units, during removal of 5'-protecting groups (detritylation). In this process the bond between the heterocyclic base and the deoxyribose unit is cleaved.

After synthesis, all protecting groups are removed and the oligonucleotide is cleaved from the solid support (Ref. 1). This is normally done by heating in concentrated aqueous ammonia at 50°–60° C. for several hours. During this treatment the chains will be cleaved at the points of depurination, thus generating shorter sequences. This can in turn cause serious problems during purification. Purification of oligonucleotides can be done by different methods of which electrophoresis and chromatography are the predominant techniques used. Both ion exchange (IEX) and reversed phase chromatography (RPC) are powerful tools in this process. In RPC there are two basic alternatives namely trityl-on and trityl-off chromatography. In the first case the 5'-protecting groups (DMTr) is left intact at the end of the assembly. It is stable during deprotection and conditions used for purification. It is, due to the aromatic ring system, extremely hydrophobic in comparison with the oligonucleotide, and it can therefore be used as a hydrophobic handle during RPC purification. The product carrying DMTr will elute at a much higher concentration of organic modifer ($CH_3CN$ or ethanol) than the corresponding product without DMTr. Unfortunately, shorter fragments also carrying DMTr are always found in the product mixture. They are formed either as a consequence of chain cleavage at points of depurination as described earlier or as a consequence or random chain cleavage during deprotection. The presence of these shorter fragments with DMTr cause problems during purification using trityl on RPC-chromatography.

By using a chromatography system which can generate a gradient it is possible to obtain a pure product for sequences of at least 100 bases in length. After collection of the product fraction the DMTr-group can be removed by treatment with acetic acid.

The present invention refers to a new way of attaching the first nucleoside to the solid support which is stable to the deprotection conditions but cleavable with a specific reagent. In this case all shorter fragments with DMTr formed during deprotection are easily removed by washing the support while the full-length product, also with DMTr, will still be immobilized. After cleavage from the solid support the product will be very simple to purify by RPC.

The present invention provides a unique solid support system especially useful in the synthesis of oligonucleotides. Specifically, the system of the present invention is characterized by its unique way of attaching the first nucleoside to the solid support. The stability of the linkage to the support is such that it is stable to all reagents used in the process, that is not only for synthesis but also for deprotection. It is nevertheless cleavable by use of very specific reagents. The parent 3'-hydroxy compound will be formed in the process. The system of the present invention is unique in several ways. It is not only a highly efficient system for synthesis of oligonucleotides but it also greatly simplifies the process of purification by trityl-on reversed phase chromatography. The reason for the simplified purification is due to the fact that the most difficult contaminants from a trityl-on RPC purification point of view (shorter fragments with DMTr) are cleaved from the solid support during the deprotection step. Since the full-length product (also with DMTr) is anchored to the support these contaminants can be removed by a simple washing procedure. The process of purification will in this case be simplified to that of separation of fragments without DMTr from the full-length product with DMTr. This can be achieved by using a very simple type of chromatography equipment consisting of a disposable RPC-carriage and buffers. This should be compared with the need to use a complex chromatography instrument when a conventional support system is used. The use of the new support system will also greatly reduce the time needed to perform the purification step. The present invention provides much more versatility than previously known support systems. The system is compatible with all oligonucleotide synthesis methods (both DNA and RNA) available today. It permits oligonucleotides to be completely deprotected while still anchored to the support.

Supports with immobilized oligonucleotides can in this form be used as hybridization affinity matrices. Some possible applications of such supports are: purification of mRNA, solid phase cDNA synthesis, purification of DNA-binding proteins, affinity purification of plasmids, as a support for gene assembly (from oligonucleotides) etc.

Even though the linkage between the first nucleoside and the support is completely stable to all synthesis and deprotection reagents, which includes both mild acid (detritylation with TCA/DCA) and mild base (deprotection with ammonia) it can still be cleaved selectively without affecting the oligonucleotide. This process is essentially quantitative.

The solid support system of the present invention comprises a solid support and a nucleoside covalent bonded to said support wherein the nucleoside can be selectively cleaved from the support by the action of a tetralkyl ammonium fluoride (Naked fluoride ion).

In the new support system of the present invention the first nucleoside is bound to the support via a silylether linkage and the system is preferably represented by the following formula (1).

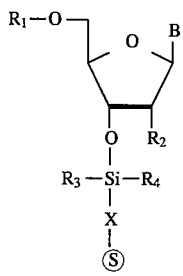

Wherein B is a nucleoside or deoxynucleoside base; $R_2$ is —H, —OH, or $OR_5$ in which $R_5$ is a protecting group; $R_1$ is a protecting group; $R_3$ and $R_4$ taken separately each represent alkyl, aryl, cykloalkyl, alkenyl, aralkyl, cycloalkylalkyl, alkyloxy, aryloxy, cycloalkyloxy, alkenyloxy and aralkyloxy; X is an anchoring group used for covalent bonding to the support which is represented by alkyl, aryl, cycloalkyl, alkenyl, aralkyl, cycloalkylalkyl, alkyloxy, aryloxy, cycloalkyloxy, alkenyloxy, aralkyloxy and cycloalkylalkyloxy; and S is a solid support. Taken together maximally one of $R_3$, $R_4$ and X-S represent alkyloxy, aryloxy, cycloalkyloxy, alkenyloxy, aralkyloxy, and cycloalkylalkyloxy. Preferred are systems where $R_1$ is a trityl, monomethoxy trityl, dimethoxytrityl or pixyl, group B is preferably adenine, guanine, cytosine, uracil, thymine, or inosine. Preferred are also systems in which one of $R_3$, $R_4$ and X-S is a tertiary alkyl or tertiary alkyloxy group, especially with $\leq 10$ carbon atoms. The other two of $R_3$, $R_4$ and X-S are preferably alkyl, aryl, alkyloxy, or aryloxy groups.

The oligonucleotide synthesis method of the present invention comprises (a) selection of a solid support (b) attachment of the first nucleoside via a silylether according to formulae 1 (c) blocking of excess reactive groups on the solid support (d) condensation of nucleotides onto the first nucleoside on the support to synthesize an oligonucleotide (e) removal of all protecting groups on the oligonucleotide except the 5'-protecting group, for instance a 5'-dimethoxytrityl group and cleavage of apurinic sites formed during acid-catalysed deprotection (f) selective cleavage of the oligonucleotide from the support by reaction for instance with a tetraalkylammonium fluoride or hydroxide and (g) purification of the oligonucleotide by reversed phase chromatography, using the 5'-protecting group as an affinity handle.

The present invention accordingly provides a unique solid support system that enables convenient and versatile synthesis and purification of oligonucleotides. It comprises a solid support and a silylated nucleoside covalently bound to said support via one of the silicon substituents.

The development of this solid support system is of particular significance. It enables convenient synthesis of oligonucleotides and facilitates purification of full length products. The purification is simplified since contaminants that are formed as a consequence of acid-catalysed depurination during synthesis are removed while the product is still anchored to the support. This occurs during the deprotection step when all groups protecting different functions of the oligonucleotide is removed, after synthesis has been completed. The product can at this stage be cleaved selectively by the action of tetraalkylammonium fluorides or hydroxides and purified by chromatography on a simple RPC-cartridge. In addition, this solid support system can be used to facilitate the immobilization of DNA or RNA complementary to the sequence synthesized on the support. The large number of application of the solid support system from an affinity matrix point of view will be apparent to one skilled in the art.

A wide range of porous as well as non-porous solid supports can be used as supports in methods according to the present invention. The group of preferred supports includes organic as well as inorganic materials and comprises polystyrenes, cross-linked polystyrenes, silica, polysaccharides, crosslinked polysaccharides and various glasses.

The solid supports should of course be stable to conditions used for oligonucleotide synthesis and deprotection. They are derivatised to contain reactive groups necessary to effectuate covalent bonding of a nucleoside silyl ether via one of the silicon substituents. Reactive groups that can be used for this purpose are for instance hydroxyl, carboxyl amino, and thiol groups. Hydroxyl groups on the support may be reacted with a chlorosilane function of a derivatised nucleoside. Alternatively the support can be derivatised with amino groups which can be reacted with a carboxyl or epoxy group of one of the silicon substituents of the derivatised nucleoside. There are many other methods of attaching the silylated nucleoside to the support via one of the silicon substituents. This can be radily realized by one of ordinary skill in the art. Before the solid support system can be used to synthesize oligonucleotides, reactive groups must be blocked on the support as well as the nucleoside. This is important in order to avoid side reactions during synthesis. In the case of the nucleoside this is easily accomplished by converting the exocyclic amines to amides or amidines and the 5'-hydroxyl group to the corresponding dimethoxytritylether. Blocking of the reactive groups on the support will be dependent on the support system employed and will be apparent to one of ordinary skill in the art.

The solid support system of the present invention may have many embodiments. All of these however have one feature in common. They have a linkage between the first base and the solid support which is a silyl ether which can be cleaved by the action of tetralkylammonium fluorides (or their known equivalents), according to formulae (1):

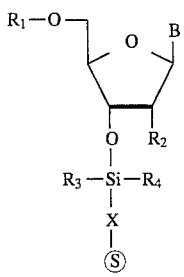

Wherein B is a nucleoside or deoxynucleoside base; $R_2$ is —H, —OH, or $OR_5$ in which $R_5$ is a protecting group; $R_1$ is a protecting group; $R_3$ and $R_4$ taken separately each represent alkyl, aryl, cykloalkyl, alkenyl, aralkyl, cycloalkylalkyl, alkyloxy, aryloxy, cycloalkyloxy, alkenyloxy and aralkyloxy; X is an anchoring group used for covalent bonding to the support which is represented by alkyl, aryl, cycloalkyl, alkenyl, aralkyl, cycloalkylalkyl, alkyloxy, aryloxy, cycloalkyloxy, alkenyloxy, aralkyloxy and cycloalkylalkyloxy; and S is a solid support. Taken together maximally one of $R_3$, $R_4$ and X-S represent alkyloxy, aryloxy, cycloalkyloxy, alkenyloxy, aralkyloxy, and cycloalkylalkyloxy. Preferred are systems where $R_1$ is a trityl, monomethoxy trityl, dimethoxytrityl or pixyl group, B is preferably adenine, guanine, cytosine, uracil, thymine, or inosine. Preferred are also systems in which one of $R_3$, $R_4$ and X-S is a tertiary alkyl or tertiary alkyloxy group. The other two of $R_3$, $R_4$ and X-S are preferably alkyl, aryl, alkyloxy, or aryloxy groups. Preferred systems of the present invention are exemplified but not limited to the following systems.

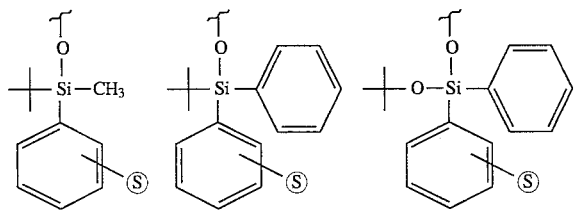

-continued

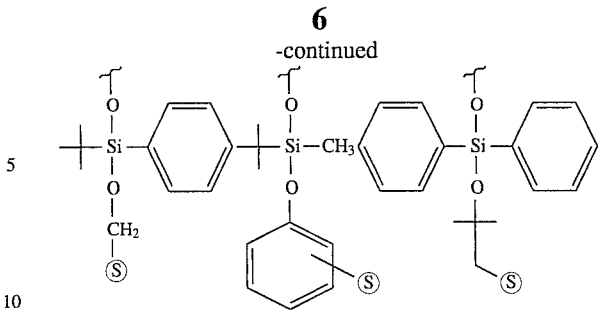

The present invention is illustrated by the following examples.

EXAMPLE 1

Synthesis of 5'-O-Dimethoxytrityl-3'-O-(tert butyl-4-glycidoxyphenyl-phenyl)-silyl-2'-deoxythymidine and its attachment to a solid support derivatised with amino groups.

P-allyloxyphenyl-t-butyl-phenyl-chlorosilane (1)

4-Bromophenyl-allylether (4,26 g, 20 mmol) was dissolved in 1,2-dimethoxyethane (40 ml) under a nitrogen atmosphere. The mixture was cooled to −78° C. (dry-ice/ethanol) and butyllithium (1,6M in hexane, 20 mmol) was added while stirring by pressurising the butyllithium-bottle with dry nitrogen. Soon after the addition a white precipitate was formed (4-lithio-phenyl-allyl-ether). After 30 min t-butyl-phenyldichlorosilane (4,66 g, 20 mmol) was added and the mixture was slowly allowed to reach room temperature. The resulting mixture was filtered over dry sodium sulfate (to remove lithium chloride) and evaporated to dryness on a rotary evaporator. The resulting oil was purified by fractional distillation, bp 147°–155° C. (1 mm Hg), yield: 1,88 g (38%).

5-O-Dimethoxytrityl-3'-O(allyloxyphenyl-t-butyl-phenyl)-silyl-2'-deoxythymidine (2)

5'-O-dimethoxytrityl-2-deoxythymidine (1,09 g, 2,0 mmol) and imidazole (0,27 g, 4,0 mmol) was coevaporated twice with dry pyridine (10 ml). The mixture was then dissolved in dry pyridine (25 ml). The monochlorosilane (1,0 g, 3,0 mmol) was added and the reaction was allowed to proceed at 50° C. over night. The reaction was followed by TLC (toluene/ethylacetate 1:1).

The reaction mixture was evaporated to dryness, dissolved in methylene chloride, washed with 10% sodiumbicarbonate, dried over sodium sulfate, filtered and evaporated. The resulting syrup was purified by flash chromatography (toluene/ethylacetate 3:1 containing 1% pyridine). Yield: 1,50 g (89,5%).

5'-O-Dimethoxytrityl-3'-O-(tert-butyl-p-glycidoxyphenylphenyl)-silyl-2'-deoxythymidine (3)

5'-O-Dimethoxytrityl-3'-O-((p-allyloxyphenyl)-tert-butyl-phenyl)-silyl-2'-deoxythymidine (0,50 g, 0,60 mmol) was dissolved in chloroform (10 ml). Sodium bicarbonate (100 mg) was added to the stirred mixture followed by m-chloroperbenzoic acid (85%, 120 mg, 0,60 mmol). The reaction was allowed to proceed at room temperature for several days. The mixture was diluted with chloroform and washed with 0,1M sodium hydroxide, 0,5M sodium bicarbonate, dried over sodium sulfate, and evaporated.

The residue was then purified by flash chromatography (toluene-ethylacetate 4:1, containing 1% pyridine). Yield: 52 mg (10%) as a mixture of stereoisomeres.

Attachment of glycidylether (3) to a solid support derivatised with primary amino Glycidylether (3) (15 mg) was dissolved in ethanol (6 ml). This solution was added to amino derivatised polystyrene beads (500 mg, 200 μmol NH$_2$/g). The suspension was shaken at 40° C. over night. The support was filtered and washed with ethanol (50 ml) and acetonitrile (50 ml).

The support was suspended in acetonitrile (10 ml), and a mixture of 4-dimethylaminpyridine (3% W/V), acetic anhydride (10% V/V) and sym-collidine (15% V/V) in acetonitrile (10 ml) was added in order to block excess primary amino groups on the support and the secondary amino groups generated by aminolysis of the glycidyl ether. After 30 min at room temperature the support was washed with acetonitrile, ethanol, and dried with diethylether. Dimethoxytrityl release from the support indicated a degree of substitution of 5,7 μmol/g.

EXAMPLE 2

Synthesis of 5'-O-Dimethoxytrityl-3'-O((p-glycidoxyphenyl)-tert-butyl-methyl)-silyl-2'-deoxythymidine and its attachment to a solid support derivatised with amino groups.

P-allyloxyphenyl-t-butyl-methyl-chlorosilane (5)

4-Bromophenyl-allylether (8,7 g, 41 mmol) was dissolved in dry 1,2-dimethoxyethane (100 ml) under an atmosphere of dry nitrogen. The mixture was cooled to −78° C. (dry-ice-ethanol). Butyllithium (1,6M in hexane, 40 mmol) was added by pressurising the butyllithium bottle with dry nitrogen. Soon after the addition a white precipitate was formed (4-lithio-phenyl-allylether). After 30 min tert-butyl-methyl dichlorosilane (3,4 g, 20 mmol) was added dissolved in 1,2-dimethoxyethane. The mixture was allowed to reach room temperature slowly. The solution was filtered over Na$_2$SO$_4$, and evaporated to dryness. The residue was purified by fractional distillation to give the title compound (5). Yield: 4,2 g b.p. 91°–95° C.

5'-O-Dimethoxytrityl-3'-O((p-allyloxyphenyl)-tert-butylmethyl)-silyl-2'-deoxythymidine (6)

5'-O-Dimethoxytrityl-2'-deoxythymidine (1,0 g, 1,8 mmol) and imidazole (260 mg, 3,9 mmol) was coevaporated twice with dry pyridine (10 ml). The residue was dissolved in dry pyridine (25 ml) and monochlorosilane (5) was added (0,73 g, 2,7 mmol). The reaction was allowed to preceed at 50° C. over night. The reaction mixture was evaporated to dryness, dissolved in methylene chloride, washed with sodiumbicarbonate (10%), dried over sodium sulfate, filtered, and evaporated. Purification by flash chromatography (toluene: ethyl acetate 3:1 containing 1% pyridine gave (6), 0,28 g (18%). The yield was low due to loss of 5'-Dimethoxytrityl-groups during evaporation prior to purification (evaporator contaminated).

5'-O-Dimethoxytrityl-3'-O(tert-butyl-(p-glycidoxy-phenyl)-methyl)-silyl-2'-deoxythymidine (7)

5'-O-Dimethoxytrityl-3'-O((p-allyloxyphenyl)-t-butyl-methyl)-silyl-2'-deoxythymidine (50 mg, 64 μmol) was dissolved in chloroform (1 ml). Sodiumbicarbonate (11 mg, 130 μmol) and m-chloroperbensoic acid (85%, 13 mg, 64 μmol) were added and the reaction mixture was stirred at room temperature for several days (weekend). The reaction mixture was diluted with chloroform, washed with sodium hydroxide (0,1M), washed with sodium bicarbonate (0,5M), dried over sodium sulfate, filtered and evaporated to dryness. The residue was purified by flash chromatography to give (7) as a stereoisomeric mixture. Yield: 4,6 mg (9%).

Attachment of glycidylether (7) to a solid support derivatised with amino

Glycidylether (7) (4,6 mg) was dissolved in ethanol (2 ml) and added to amino derivatised polystyrene beads (162 mg). The reaction was allowed to proceed at 40° C. over night. The support was filtered and washed with ethanol and acetonitrile. The support was suspended in acetonitrile (3 ml) and a mixture of 4-dimetyl-aminopyridine (3% W/V), acetic anhydride (10% V/V), collidine (15% V/V) in acetonitrile (3 ml) was added. After shaking at room temperature for 30 min the support was filtered, washed with acetonitrile, ethanol and dried with diethylether. Dimethoxytrityl release from the support indicated a degree of substitution of 5,0 μmol/g.

EXAMPLE 3

Synthesis of 5'-O-Dimethoxytrityl-3'-O-(tert-butyl-imidazolyl-phenyl)-silyl-2'-deoxythymidine and its attachment to a solid support derivatised with hydroxyl groups (9).

5'-O-Dimethoxytrityl-2'-deoxythymidine (100 mg, 0,18 mmol) and imidazole (35 mg, 0,5 mmol) was coevaporated twice with dry pyridine (5 ml). The residue was dissolved in dry pyridine (2,0 ml). After addition of t-butyl-phenyldichlorosilane (38 μl, 0,18 mmol) the reaction was allowed to proceed at room temperature for 2 h when TLC (toluene: ethyl acetate 1:1) revealed that the reaction was complete. The reaction mixture was added to polystyrene beads derivatised with hydroxyl groups (500 mg) which had previously been washed with pyridine. The reaction mixture was shaken over night at room temperature. The support was filtered and washed with pyridine, ethanol and dried with diethylether.

It was then treated with a mixture of 4-dimethyl-aminopyridine (3% W/V), acetic anhydride (10% V/V) and sym collidine (5% V/V) in acetonitrile (4 ml). After 15 min at room temperature the support was washed with acetonitrile, ethanol, and dried with diethylether. Dimethoxytrityl release from the support indicated a degree of substitution of 27 μmol/g.

EXAMPLE 4

Synthesis of 5'-O-dimethoxytrityl-3'-O-(tert-butyl-(3-chloro-propyl)-methyl)-silyl-2'-deoxythymidine and its attachment to a support derivatised with aminogroups.

Tert-butyl-3-chloropropyl-methyl-chlorosilane (10)

3-chloropropyl-methyl-dichlorosilane (4,0 ml, 25 mmol) was dissolved in dry petroleum ether (20 ml) and cooled to 0° C.

Tert-butyl lithium (1,7M in pentane, 15 ml, 25 mmol) was added under an atmosphere of dry nitrogen. After the addition the reaction mixture was allowed to reach room temperature. After 1 h the reaction mixture was filtered over dry sodium sulfate (removal of lithium chloride) and evaporated. Fractional distillation afforded pure (10), 3,9 g (73%), bp: 68°–72° C. (5 mm).

5 '-O-Dimethoxytrityl-3'-O-(tert-butyl-(3-chloropropyl)-methyl)-silyl-2'-deoxythymidine (11)

5'-O-Dimethoxytrityl-2'-deoxythymidine (545 mg, 1 mmol) was evaporated twice with dry pyridine (5 ml). The residue was dissolved in dry pyridine (3 ml). Imidazole (150 mg, 2,2 mmol) and tert-butyl-(3-chloropropyl)-methyl-chlorosilane (23 mg, 11 mmol) was added and the reaction mixture was stirred at 50° C. over night. The mixture was evaporated to dryness and purified by flash chromatography (toluene: ethyl acetate 3:1 containing 1% pyridine) to give pure (11), 0,54 g (75%) as a mixture of stereoisomeres.

Attachment of 3-chloropropyl-silyl ether (11) to a support derivatised with amino groups The 3-chloropropyl-silyl ether (11) (15 mg, 20 μmol) was dissolved in N,N-dimethyl formamide (0,5 ml) containing a catalytic amount of tetra n-butyl-ammonium Iodide. This solution was added to a solid support derivatised with amino groups polystyrene beads (100 mg). The mixture was shaken at 50° C. over night. The support was filtered and washed with DMF, methanol, and dried with diethylether. It was then treated with a mixture of 4-dimethyl amino pyridine (3% V/V), acetic anhydride (10% V/V and sym-collidine (15% V/V)) in acetonitrile (4 ml). After 15 min at room temperature the support was filtered and washed with acetonitrile, ethanol and dried with diethyl ether. Dimethoxytrityl release from the support indicated a degree of substitution of 8 μmol/g.

EXAMPLE 5

Synthesis, deprotection and cleavage of oligonucleotides on support (4)

Support (4) was packed in reaction columns for use in Gene Assembler™ Plus (20 mg, 0,11 μmol). Oligonucleotides were synthesized using the standard 0,2 μmol reaction cycle using PAC-amidites. Average coupling efficiencies were in the range of 99,0–99,5% as judged by dimethoxytrityl release in the beginning on each cycle. The dimethoxytrityl group at the 5'-end was left intact after completion of the synthesis. The reaction column was placed in an Eppendorf tube and centrifuged for 1–2 min at 3000 rpm in order to dry the support. Concentrated ammonia (1,0 ml) was added and the tube was centrifuged once more in order to let the liquid penetrate the interior of the reaction column. The tube was heated at 70° C. for 60 min. The reaction column was placed in a second tube and centrifuged. The ammonia solutions were combined and analysed by reversed phase chromatography. It contained besides the protecting groups the shorter oligomeres carrying DMTr-Groups resulting from cleavage of the apurinic sites formed during synthesis. The column reactor was washed with water, ethanol and dried with diethyl ether. Cleavage of the oligonucleotide from the support was accomplished by treatment with either 0,1 m TBAF in DMF (1,0 ml) at 70° C. for 30 min or 1,0M NaOH (1,0 ml) at 70° C. for 15 min.

EXAMPLE 6

Purification of an oligonucleotide (18-mer) made on support (4) after cleavage with 0,1M TBAF in DMF The TBAF solution (1,0 ml) was applied to an anion exchange column (Mono Q®) which had been equilibrated with 0,5M NaCl. After washing with 0,5M NaCl (removal tetrabutylammonium ions and DMF) the oligonucleotide mixture was eluted with 3,0M NaCl (2,5 ml). An aliquot of this mixture was analysed by reversed phase chromatography. Purification was accomplished using a disposable RPC cartridge, and comprised the following steps:

1. Loading of the oligonucleotide.
2. Washing with acetonitrile (16,5%) in 0,1M triethyl ammonium acetate, pH 7,0. This removes all material without DMTr-groups.
3. Washing with water.
4. Treatment with 1% TFA/$H_2O$ for 4 min. in order to remove the 5'-DMTr-group.
5. Washing with water.
6. Elution of the product with acetonitrile (16,5%) in 0,1M triethyl ammonium acetate, pH 7,0.

The purified material was then analysed by RPC, to give a homogenous product.

EXAMPLE 7

Purification of two oligonucleotides (20 and 50-meres) made on support (4) after cleavage with 1,0M NaOH Aliquots of the NaOH-solutions were analysed directly by reversed phase chromatography. The 50-mere was purified using a disposable RPC-cartridge (see Example 6). The purified material was then analysed by reversed phase chromatography to give a nearly (>97%) homogenous product.

REFERENCES

1. R. W. Ellis, Pharmaceutical Research. 3 (1986) 195.
2. J. W. Engels, E. Uhlmann, Angew. Chem. Int. Ed. Engl. 28 (1989) 716.
3. G. Zon, Pharmaceutical Research. 5 (1988) 539.
4. M. J. Gait, Oligonucleotide synthesis—a practical approach, IRL press, Oxford, England.
5. R. B. Merrifield, J. Am. Chem. Soc. 85 (1963) 2149.
6. S. L. Beaucage, M. H. Caruthers, Tetrahedron Lett. 22 (1981) 1859.
7. N. D. Sinha, J. Biernat, H. Köster, Tetrahedron Lett. 24 (1983) 5843.
8. J. C. Shulhof, D. Molko, R. Teoule, Nucleic Acids Res. 15 (1987) 397.
9. B. C. Froehler, P. G. Ng, M. D. Matteucci, Nucleic Acids Res. 14 (1986) 5399.
10. P. J. Garegg, I. Lindh, T. Regberg, J. Stawinski, R. Strömberg, C. Henrichsson, Tetrahedron Lett. 27 (1986) 4051.
11. A. M. Michelson, A. R. Todd, J. Chem. Soc. (1955) 2632.
12. H. Schaller, H. G. Khorana, J. Am. Chem. Soc. 85 (1963) 3828.

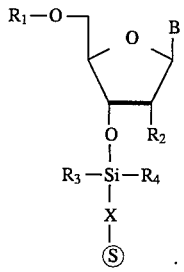

I claim:

1. A support for the synthesis of oligonucleotides consisting of a solid support having a first nucleoside bound thereto, wherein said first nucleoside is bound to said support via a silylether linkage directly to said first nucleoside, said silylether linkage being stable to synthesis and deprotection reagents and selectively cleavable by a silylether cleaving agent.

2. The support system according to claim 1, wherein said support system is represented by the formula:

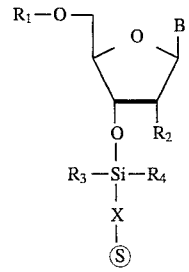

wherein

B is a nucleoside or deoxynucleoside base, $R_1$ is a protecting group, $R_2$ is —H, —OH, or —$OR_5$ wherein $R_5$ is a protecting group, $R_3$, $R_4$ and X each represent alkyl, aryl, cycloalkyl, alkenyl, aralkyl, cycloalkylalkyl, alkyloxy, aryloxy, cycloalkykyloxy, alkenyloxy, or aralkyloxy, and S is a solid support, whereby not more than one of $R_3$, $R_4$ and X represent alkyloxy, aryloxy, cycloalkyloxy, alkenyloxy, aralkyloxy or cycloalkylalkyloxy.

3. The support system according to claim 2, wherein $R_1$ is trityl, monomethoxy trityl, dimethoxytrityl or pixyl, B is adenine, guanine, cytosine, uracil, thymine, or inosine.

4. The support system according to claim 2, wherein $R_3$ is an aryl group,

X is an alkyl or alkyloxy chain, and $R_4$ is a tertiary alkyl or tertiary alkyloxy group.

5. The support according to claim 1, wherein said $R_3$ and $R_4$ alkyl groups are $\leq C_{10}$.

6. A method for synthesizing oligonucleotides on a solid support, wherein said solid support has a first nucleoside bound thereto via a silylether linkage directly to said first nucleoside, said silylether linkage being stable to synthesis and deprotection reagents and selectively cleavable by a silylether cleaving agent which comprises:

(i) condensing protected nucleotides onto said first nucleoside thereby forming a desired oligonucleotide in protected form, each condensation of a nucleotide being preceded by an acid catalyzed 5'-deprotection step;

(ii) removing all protecting groups on said protected oligonucleotide except for a 5'-protecting group and cleaving any apurinic sites which may have been formed during acid-catalyzed 5'-deprotection in step (i);

(iii) cleaving said silylether linkage by a silylether cleaving agent to remove said oligonucleotide from said support; and (iv) purifying said oligonucleotide by reverse phase chromatography, using said 5'-protecting group as an affinity handle.

7. The method according to claim 6, wherein said 5'-protecting group is dimethoxytrityl.

8. The method according to claim 7, wherein said cleavage reaction (iii) is carried out by using tetra-alkylammonium fluoride or hydroxide.

9. The method according to claim 6, wherein said support system is represented by the formula: